United States Patent [19]

Tuvell

[11] 4,347,381
[45] Aug. 31, 1982

[54] METHOD OF TREATING LONG CHAIN ALKYL AMINES OR PRODUCTS DERIVED THEREFROM

[75] Inventor: Melvin E. Tuvell, Baton Rouge, La.

[73] Assignee: Ethyl Corporation, Richmond, Va.

[21] Appl. No.: 871,811

[22] Filed: Jan. 24, 1978

[51] Int. Cl.$^3$ .............................................. C07C 85/26
[52] U.S. Cl. ....................................... 564/2; 560/155; 564/282; 564/291; 564/297; 564/299; 564/437; 564/463
[58] Field of Search .............. 260/702, 583 N, 583 D, 260/501.11, 567.6 M, 582, 575; 564/2, 497, 463

[56] References Cited

U.S. PATENT DOCUMENTS

| | | | |
|---|---|---|---|
| 1,947,578 | 2/1934 | Bond et al. ..................... | 260/575 X |
| 2,369,757 | 2/1945 | Schmidt .......................... | 260/702 X |
| 3,006,934 | 10/1961 | Dieckelmann .................. | 260/582 X |
| 3,168,569 | 2/1965 | Matell ............................. | 260/582 X |
| 3,215,741 | 11/1965 | Chadwick ....................... | 260/583 D |

Primary Examiner—John Doll
Attorney, Agent, or Firm—Donald L. Johnson; John F. Sieberth; Paul H. Leonard

[57] ABSTRACT

The pink color content often produced in products such as amine salts, amine oxides, betaines, quaternary ammonium compounds or other compounds derived from long chain alkyl amines is eliminated by treating the products with trace amounts of a bleaching agent. Heating of the treated amine at relatively low temperatures for a short period of time enhances the effectiveness of the bleaching agent. Long chain alkyl amines having a pink color may be similarly treated.

7 Claims, No Drawings

METHOD OF TREATING LONG CHAIN ALKYL AMINES OR PRODUCTS DERIVED THEREFROM

BACKGROUND OF THE INVENTION

The present invention relates to a process for treating or refining products or compounds derived from amines or amines themselves. More particularly, it relates to a process comprising treating products derived from aliphatic amines with a bleaching agent to eliminate any pink color therein.

The invention primarily relates to the treatment of amine salts, amine oxides, betaines and quaternary ammonium salts and other compounds derived from long chain alkyl amines to eliminate the pink color characteristic of such compounds when so derived.

Long chain alkyl amines are customarily produced from fatty acids or alcohols or from an intermediate raw material derived from petroleum products, particularly low polymers of ethylene such as materials well known in the art as α olefins and Ziegler alcohols. The products of such amines particularly those of the latter often have a characteristic pink color which is objectionable to some manufacturers of derivative products, especially quaternary ammonium salts. The long chain alkyl amines also display this same pink color upon acdification.

Long chain alkyl amines, such as alkyl dimethylamines are widely used as cationic surfactants and as chemical intermediates for the manufacture of quaternary ammonium compounds, amine oxides, and betaines. These products are used as biocides, disinfectants, sanitizers, textile additives, corrosion inhibitors and surfactants.

One solution to the colorization problem is illustrated by Takaku et al U.S. Pat. No. 3,922,306. In this patent, small amounts of alkali metal borohydrides are added to long chain aliphatic hydrocarbon amines to inhibit undesirable color formation in derivation products. Although such refining is usually effective, such borohydrides are very expensive.

U.S. Pat. No. 3,595,921 issued to Pitts in 1971 discloses a color problem with polyethylene polyamine products and a solution for such problem by treating such products with potassium hydroxide. The patentee also discloses that fractional distillation of the product and other techniques such as treatment with activated carbon, sodium borohydride, mixtures of calcium hypochlorite and calcium hydroxide, hydrochloric acid, or oxidation of impurities with potassium dichromate, have all failed to reduce the color content of polyethylene polyamine products.

It is therefore a primary object of the present invention to provide an effective and inexpensive treatment of pink colored amines and pink colored derivation products of amines to reduce or eliminate the undesirable pink color content of such amines or products.

Another object of the invention is to reduce or eliminate the characteristic pink color in acidified long chain alkyl amines prepared from petroleum products.

Another object of the invention is to reduce or eliminate the characteristic pink color in amine compounds derived from long chain alkyl amines prepared from petroleum products, especially such pink color in amine derivatized alkyl benzyl quaternary ammonium chloride salts.

Other objects and advantages of the present invention will become more readily apparent from a consideration of the description hereinafter.

SUMMARY OF THE INVENTION

The present invention relates to an improved process for treating compounds derived from aliphatic amines or acidified aliphatic amines by treating said compounds or amines with relatively small or trace amounts of a bleaching agent.

The invention particularly relates to a method of eliminating the pink color in products derived from long chain alkyl amines by treating the products with relatively small or trace amounts of a bleaching agent. The invention also relates to a bleaching agent. The invention also relates to a method of similarly treating pink colored long chain alkyl amines.

DESCRIPTION OF THE PREFERRED EMBODIMENT

The instant invention is a method of treating pink colored products derived from aliphatic hydrocarbon amines having at least one alkyl group of 8 to 22 carbon atoms attached to the amino nitrogen or treating pink colored amines which comprises eliminating or substantially reducing the pink color by treating the derivatized products or amines with trace amounts of a bleaching agent. Typical products derived from such amines are amine salts, amine oxides, betaines, and quaternary ammonium salts. Any of such products or any other compounds derived from such amines which have a pink color content may be similarly treated.

Suitable bleaching agents for use in the instant invention are hydrogen peroxide, sodium bisulfite, sodium sulfite, sodium thiosulfate and sodium hypochlorite or the like, with hydrogen peroxide being the most preferred. As little as 0.01 grams of the bleaching agent is sufficient for some color reduction. Heating at relatively low temperatures of 30°–70° C. for a short period of time enhances the effect of the bleaching agent.

Heating times vary with the particular bleaching agent used. Usually as little as five minutes produces a marked decrease in color. Heating periods of up to about 30 minutes are normally sufficient to achieve adequate reduction in color.

Although temperatures of from about 40°–60° C. are preferred, some bleaching agents, for example sodium hypochlorite are effective at ambient temperatures. In general, temperatures of from 40°–60° C. show little change in color reduction; however, a significant decrease in bleaching is noted about 30° C.

It should be noted that the invention is directed to the removal or elimination of the pink color in the aforementioned compounds. Not all compounds derived from long chain alkyl amines have a pink color. Although not wishing to be bound by any particular theory, it is believed that the pink color in products derived from long chain alkyl amines may be attributed to unreacted amine in the product. Products produced from petroleum derived amines are more likely to exhibit this characteristic pink color. Products produced from fatty acids or alcohols sometimes display a pink color.

Long chain alkyl amines, e.g. alkyl dimethyl amine, do not exhibit a pink color after manufacture. The pink color occurs in the products produced from the amines. The pink color can be produced directly in the amines themselves by acidifying the amine with hydrochloric acid or other suitable acid to a pH of 5 or less and then heating the amine at relatively low temperature, up to about 100° C. for up to about one hour. Once the pink color has been formed in the amine, the pink color can be eliminated by treating the amine with a relatively small amount of bleaching agent. Products derived from pink colored amines treated with a bleaching agent to remove the pink color exhibit a very slight pink color. Treatment with a bleaching agent of an amine in which the pink color had not been obtained produced no noticeable effect in a product derived from the amine. Such product exhibited the characteristic pink color. The pink color in the product was removed by treatment with a bleaching agent. The invention is therefore directed to the treatment of pink colored amines or pink colored products or compounds produced or derived from amines. The treatment with small amounts of bleaching agent has no deleterious effect on either the products derived from the amines or the amines.

To effect an empirical comparison of bleaching agents or reagents under various conditions, a method for determining pink intensity was developed. Simple colormetric analysis via customary instrumental means was unsuitable because of interferences in the visible and ultra-violet spectra of long chain alkyl quaternary ammonium salts.

Pink color in the acidic ADMA (alkyl dimethyl amine) quats is complicated by a background yellow tint in the solutions. The yellow color is present throughout the normal pH ranges observed (pH 3 to 10). To eliminate the yellow influence during the pink comparison, a standard color wheel was selected (Varnish No. 620C-40). A sample, at pH>5, was prepared at an appropriate concentration and its attendant yellow color was matched to the color wheel. The yellow filter selected was then added to a set of pink samples (aqueous cobalt chloride) or known intensity. The combinant color (pink-orange) standards were then compared to a sample (pH<3) for a direct match in hue and intensity. This experimental procedure was as follows:

DETERMINATION OF PINK COLOR IN ADMA QUATERNARY SALTS

Application

This procedure was used on ADMA quaternary salts to check intensity of pink color at low pH values.

Method

The test was an empirical one designed to measure the degree of pink color which can be expected at low pH values. The test depended on the reaction of acid with trace impurities in the sample to generate a pink color body. The color generated was compared visually with a series of standards previously prepared.

Reagents 1. 2 N HCl, reagent ACS grade diluted with deionized water.
2. Cobalt chloride standards.

Apparatus

1. Water bath, maintained at 60° C.
2. Color wheel: Varnish No. 620C-40, Hellige Co.
3. Hellige comparitor and sample tube (2).
4. Two 100 ml graduated cylinders with penny stopper.
5. Volumetric Flasks: (1) 1000 ml and (10) 100 ml.
6. Transfer pipettes: 5, 10, 20, 30, 40 ml.
7. Stopwatch.

Procedure

A cobalt chloride stock solution was prepared by placing 23.793 g of cobalt chloride hexahydrate in a 1000 ml volumetric flask and diluting to the mark with deionized water. The color standards were in turn prepared by diluting 5, 10, 15, 20, 25, 30, 35, 40, 45 and 50 ml, respectively, of the stock solution to 100 ml with deionized water. These standards were identified by the number of ml stock solution utilized in each one.

25.0 ml of the neat ADMA quat (pH>5) was placed in a 100 ml cylinder and 25.0 ml of deionized water added. This was mixed gently for exactly one minute and placed in a water bath (@60° C.) for exactly 10 minutes. The sample tube was filled to the 10 ml mark with the solution and the color was matched as closely as possible. The color wheel was left in place at this setting.

A fresh sample of the ADMA quat was prepared by placing 25.0 ml of the neat quat in a 100 ml cylinder and adding 25.0 ml 2 N HCl. Mixing was as before for one minute. The sample was then placed in a water bath for 10 minutes. The sample tube was filled with the acidic quat and placed in the unfiltered light path of the comparitor. A sample tube with 10 ml of the cobalt chloride reference standard was placed in the filtered (yellow) light path. Reference standards were alternated 5 through 50 until the best hue and intensity match had been made. The numerical value of the standard was recorded.

Calculations

ADMA Pink is reported as the number of the standard.

Precision and Accuracy

The precision of this procedure is ±2.5. No accuracy figure can be quoted since the test was empirical in nature.

This procedure was used to evaluate several different reagents to determine their effectiveness in removal of the pink color body. The quaternary salt studied in all of the cases was the benzyl chloride quat of an alkydimethyl amine having the formula $CH_3(CH_2)_nCH_2N(CH_3)_2$, where n = 10, 12 and 14. The samples were 50:50 (by volume) quat and 2 N HCl with the sample size in all runs being established at 50 ml. The reagents compared (at 60° C.) were sodium bisulfite, sodium sulfite, sodium thiosulfate, sodium hypochlorite, and hydrogen peroxide. The sodium hypochlorite ("Clorox" ≈5%) and hydrogen peroxide (26.5%) were added as aqueous solutions but the other materials were added as anhydrous solids. In all runs, the pin color was developed prior to the specific treatments. The results of these tests are shown in Table I.

TABLE I

Reagent Effectiveness at 60° C.

| Heating Time (minutes) | Pink Color Intensity | | |
| --- | --- | --- | --- |
| | Sodium Sulfite (0.25g) | Sodium Bisulfite (0.25g) | Sodium Thiosulfate (0.25g) |
| 0 | 17.5 | 17.5 | 17.5 |
| 5 | 15.0 | 10.3 | 12.5 |
| 10 | 14.5 | 9.7 | 7.5 |
| 15 | 10.3 | 7.5 | 5.0 |
| 20 | 7.5 | 5.7 | 4.8 |
| 25 | 5.7 | 5.0 | 4.5 |

| | Clorox (20 drops) | Hydrogen Peroxide (15 drops) | Hydrogen Peroxide (10 drops) |
| --- | --- | --- | --- |
| 0 | 17.5 | 17.5 | 17.5 |

TABLE I-continued

| Reagent Effectiveness at 60° C. | | | |
|---|---|---|---|
| 5 | 15.0 | 12.5 | 12.3 |
| 10 | 12.5 | 5.0 | 7.5 |
| 15 | 10.3 | 1.5 | 5.3 |
| 20 | 10.0 | 0 | 4.7 |
| 25 | 9.5 | 0 | 4.3 |

TABLE II

| | Concentration Effect at 60°C. | | | |
|---|---|---|---|---|
| Heating Time | Pink Color Intensity Hydrogen Peroxide | | | |
| (minutes) | 0.009g | 0.045g | 0.090g | 0.135g |
| 0 | 17.5 | 17.5 | 17.5 | 17.5 |
| 5 | 17.5 | 16.7 | 12.5 | 7.5 |
| 10 | 17.5 | 15.0 | 7.5 | 5.0 |
| 15 | 17.5 | 12.5 | 5.7 | 1.5 |
| 20 | 15.0 | 10.0 | 5.0 | 0 |
| 25 | 14.8 | 7.5 | 4.5 | 0 |
| 30 | 14.9 | 7.3 | 1.5 | 0 |

TABLE III

| | Temperature Effect | | |
|---|---|---|---|
| Heating Time | Pink Color Intensity Hydrogen Peroxide (0.045 g) | | |
| (minutes) | 30° C. | 50° C. | 60° C. |
| 0 | 17.5 | 17.5 | 17.5 |
| 5 | 17.3 | 17.3 | 17.3 |
| 10 | 15.0 | 15.0 | 15.0 |
| 15 | 15.0 | 12.5 | 12.5 |
| 20 | 14.7 | 10.0 | 10.0 |
| 25 | 13.0 | 7.5 | 7.5 |
| 30 | 12.2 | 7.0 | 7.0 |

The foregoing disclosure and description of the invention is illustrative and explanatory thereof and various changes may be made within the scope of the appended claims without departing from the spirit of the invention.

What is claimed is:

1. A process of treating pink colored amine products derived from long chain alkyl amines or pink colored long chain alkyl amines to eliminate the pink color in said amine products or said amines, comprising the step of reacting with said amine products or said amines a color eliminating effective amount of hydrogen peroxide at a temperature of at least about 30° to about 60° C. for a period of at least about 5 minutes to about 30 minutes.

2. A process of treating pink colored amine products derived from long chain alkyl amines or pink colored long chain alkyl amines to eliminate the pink color in said amine products or said amines, comprising the step of reacting said amine products or said amines at a temperature of at least about 30° C. for a period of time of at least about 5 minutes with a color eliminating effective amount of hydrogen peroxide.

3. The process of claim 2, wherein said reactants are heated up to about 70° C.

4. The process of claim 2, wherein said long chain alkyl amines are aliphatic hydrocarbon amines having at least one alkyl group of 8 to 22 carbon atoms attached to the amino nitrogen.

5. The process of claim 2, wherein said long chain alkyl amines are petroleum derived amines.

6. The process of claim 2, wherein said long chain alkyl amines are alkyl dimethyl amines.

7. The process of claim 2, wherein said long chain alkyl amines comprise amines of the formula $$CH_3(CH_2)_nCH_2N(CH_3)_2$$

where $n = 10$, 12 and 14.

* * * * *

UNITED STATES PATENT AND TRADEMARK OFFICE
CERTIFICATE OF CORRECTION

PATENT NO. : 4,347,381

DATED : August 31, 1982

INVENTOR(S) : Melvin E. Tuvell

It is certified that error appears in the above-identified patent and that said Letters Patent is hereby corrected as shown below:

Column 4, line 48, reads "k5%", should read --∿5%--.

Column 4, line 52, reads "pin", should read --pink--.

Signed and Sealed this

Twelfth Day of April 1983

[SEAL]

Attest:

GERALD J. MOSSINGHOFF

Attesting Officer     Commissioner of Patents and Trademarks